(12) United States Patent
Kojima et al.

(10) Patent No.: US 11,093,032 B2
(45) Date of Patent: Aug. 17, 2021

(54) SIGHT LINE DIRECTION ESTIMATION DEVICE, SIGHT LINE DIRECTION ESTIMATION METHOD, AND SIGHT LINE DIRECTION ESTIMATION PROGRAM

(71) Applicant: AISIN SEIKI KABUSHIKI KAISHA, Kariya (JP)

(72) Inventors: Shinichi Kojima, Nagakute (JP); Takashi Kato, Kariya (JP)

(73) Assignee: AISIN SEIKI KABUSHIKI KAISHA, Kariya (JP)

( * ) Notice: Subject to any disclaimer, the term of this patent is extended or adjusted under 35 U.S.C. 154(b) by 81 days.

(21) Appl. No.: 16/354,849

(22) Filed: Mar. 15, 2019

(65) Prior Publication Data

US 2019/0294240 A1  Sep. 26, 2019

(30) Foreign Application Priority Data

Mar. 23, 2018 (JP) .............................. JP2018-056627

(51) Int. Cl.
| | |
|---|---|
| *G06F 3/01* | (2006.01) |
| *G06K 9/00* | (2006.01) |
| *A61B 3/113* | (2006.01) |

(52) U.S. Cl.
CPC .............. *G06F 3/013* (2013.01); *A61B 3/113* (2013.01); *G06K 9/0061* (2013.01)

(58) Field of Classification Search
CPC ........ G06F 3/013; A61B 3/113; G06K 9/0061
See application file for complete search history.

(56) References Cited

U.S. PATENT DOCUMENTS 10,296,792 B2 * 5/2019 Spizhevoy ......... G06K 9/00604
10,628,948 B2 * 4/2020 Nakazawa ............... G06T 7/00
(Continued)

FOREIGN PATENT DOCUMENTS

| EP | 2 826 414 A1 | 1/2015 |
|---|---|---|
| EP | 3 413 234 A1 | 12/2018 |

(Continued)

OTHER PUBLICATIONS

A. Villanueva and R. Cabeza, "A Novel Gaze Estimation System With One Calibration Point," in IEEE Transactions on Systems, Man, and Cybernetics, Part B (Cybernetics), vol. 38, No. 4, pp. 1123-1138, Aug. 2008, doi: 10.1109/TSMCB.2008.926606. (Year: 2008).*

(Continued)

*Primary Examiner* — Utpal D Shah
(74) *Attorney, Agent, or Firm* — Sughrue Mion, PLLC

(57) ABSTRACT

A sight line direction estimation device includes: an imaging unit that captures an image of a head portion including an eyeball of a person; an apparent sight line direction derivation unit that derives an apparent sight line direction connecting a center position of the eyeball and an apparent pupil center position on a surface of the eyeball corresponding to a pupil center position based on the image captured by the imaging unit; and a sight line direction estimation unit that estimates an actual sight line direction of the person based on a predetermined corresponding relationship between an actual sight line direction and the apparent sight line direction and the apparent sight line direction derived by the sight line direction derivation unit.

15 Claims, 9 Drawing Sheets

(56) References Cited

U.S. PATENT DOCUMENTS

| | | |
|---|---|---|
| 10,634,934 B2* | 4/2020 | Chene .................. A61B 3/0025 |
| 2015/0154758 A1 | 6/2015 | Nakazawa et al. |
| 2018/0357790 A1 | 12/2018 | Kojima et al. |

FOREIGN PATENT DOCUMENTS

| | | |
|---|---|---|
| JP | 2008-102902 A | 5/2008 |
| JP | 2011-217764 A | 11/2011 |

OTHER PUBLICATIONS

Li Sun et al., "Real-Time Gaze Estimation with Online Calibration", IEEE Multimedia, IEEE Service Center, New York, NY, US, vol. 21, No. 4, Oct. 1, 2014, pp. 28-37, XP011563649, ISSN: 1070-986X, DOI: 10.1109/MMUL.2014.54 [retrieved on Nov. 3, 2014], 10 pages total.

Extended European Search Report dated Sep. 2, 2019 issued by the European Patent Office in counterpart application No. 19164648.8.

\* cited by examiner

SIGHT LINE DIRECTION ESTIMATION DEVICE, SIGHT LINE DIRECTION ESTIMATION METHOD, AND SIGHT LINE DIRECTION ESTIMATION PROGRAM

CROSS REFERENCE TO RELATED APPLICATIONS

This application is based on and claims priority under 35 U.S.C. § 119 to Japanese Patent Application 2018-056627, filed on Mar. 23, 2018, the entire contents of which are incorporated herein by reference.

TECHNICAL FIELD

This disclosure relates to a sight line direction estimation device, a sight line direction estimation method, and a sight line direction estimation program.

BACKGROUND DISCUSSION

A technique of estimating a sight line direction of a person using a captured image obtained by capturing an image of a head portion of the person is known. For example, there proposes a technique of estimating an iris position and an eyeball position using a captured image obtained by capturing an image of a head portion of a person, and estimating the sight line direction using the estimated iris position and eyeball position (see, for example, JP 2008-102902A (Reference 1)). In this technique, an eyeball center is estimated from a plurality of images captured in a state where a posture of a face of a user is changed while the user is gazing at a camera, and a direction from the eyeball center toward an iris center is derived as the sight line direction using the estimated eyeball center and the current iris center.

As another technique of estimating a sight line direction of a person, there also proposes a technique of correcting an error of a sight line generated by each user in a case where the sight line is detected from a cornea curvature center and a pupil center obtained from a position of a reflected image on a cornea surface (see, for example, JP 2011-217764A (Reference 2)). In this technique, a sight line detection device that detects a sight line from the cornea curvature center toward the pupil center, an imaging device that captures an image of eyes of a user, and a display device are provided, the sight line toward a gaze point of a characteristic region displayed on the display device is estimated as an actual sight line, and a correction value for each user is determined.

However, in the technique of JP 2008-102902A (Reference 1), it is necessary for the user to gaze at the camera, and processing complicated in operation is required. In addition, in the technique of JP 2011-217764A (Reference 2), the sight line detection device that detects the sight line and an imaging device that captures an image of the eyes of the user are necessary, and device configurations are complex. Further, in a case where the sight line direction is estimated using the image obtained by capturing an image of the eyes of the user, it is necessary to correct a position of a characteristic portion related to a sight line of an eyeball anterior ocular segment of the user estimated from the captured image. That is, the sight line direction of the user is a direction from the eyeball center toward a center of the eyeball anterior ocular segment such as the iris center and the pupil center, but a ray refracted by a cornea of the eyeball is imaged on the image captured by the imaging device provided in a direction away from the sight line direction of the user. Therefore, it is also necessary to consider an influence caused by the refraction caused by the cornea of the eyeball. Therefore, there is room of improvement in estimating the sight line direction of the person with high accuracy.

Thus, a need exists for a sight line direction estimation device, a sight line direction estimation method, and a sight line direction estimation program which are not susceptible to the drawback mentioned above.

SUMMARY

A sight line direction estimation device according to an aspect of this disclosure includes: an imaging unit that captures an image of a head portion including an eyeball of a person; an eyeball center position calculation unit that calculates a center position of the eyeball using the image captured by the imaging unit; a pupil center position calculation unit that calculates an apparent pupil center position on an eyeball surface corresponding to a pupil center position of the eyeball using the image captured by the imaging unit; a sight line direction derivation unit that derives an apparent sight line direction in a direction connecting the eyeball center position and the apparent pupil center position; and a sight line direction estimation unit that estimates a sight line direction of the person based on the apparent sight line direction derived by the sight line direction derivation unit using a predetermined corresponding relationship between the sight line direction of the person connecting the eyeball center position and the pupil center position and the apparent sight line direction.

A sight line direction estimation method of this disclosure includes causing a computer to: calculate a center position of an eyeball using an captured image in which a head portion including the eyeball of a person is captured; calculate an apparent pupil center position on an eyeball surface corresponding to a pupil center position of the eyeball using the captured image; derive an apparent sight line direction in a direction connecting the eyeball center position and the apparent pupil center position; and estimate a sight line direction of the person based on the apparent sight line direction using a predetermined corresponding relationship between the sight line direction of the person connecting the eyeball center position and the pupil center position and the apparent sight line direction.

A sight line direction estimation program of this disclosure causes the computer to function as the sight line direction estimation device.

BRIEF DESCRIPTION OF THE DRAWINGS

The foregoing and additional features and characteristics of this disclosure will become more apparent from the following detailed description considered with the reference to the accompanying drawings, wherein:

FIGS. 5A and 5B are image diagrams illustrating an example of a schematic diagram for explaining a first derivation method of a sight line direction, wherein FIG. 5A illustrates a sight line in a modeled eyeball, and FIG. 5B illustrates a captured image obtained by capturing an image of an eye;

FIGS. 6A and 6B are image diagrams illustrating an example of a schematic diagram for explaining a second derivation method of the sight line direction, wherein FIG. 6A illustrates a sight line in a modeled eyeball, and FIG. 6B illustrates a captured image obtained by capturing an image of an eye;

DETAILED DESCRIPTION

Hereinafter, embodiments related to a disclosed technique are described with reference to the drawings.

First Embodiment

This embodiment describes an example of a case where a sight line direction of a person is estimated using a captured image obtained by capturing an image of a head portion of the person. In this embodiment, as an example of the sight line direction of the person, a sight line direction of an occupant of a vehicle such as an automobile as a moving object is estimated by a sight line direction estimation device.

Figure 1:
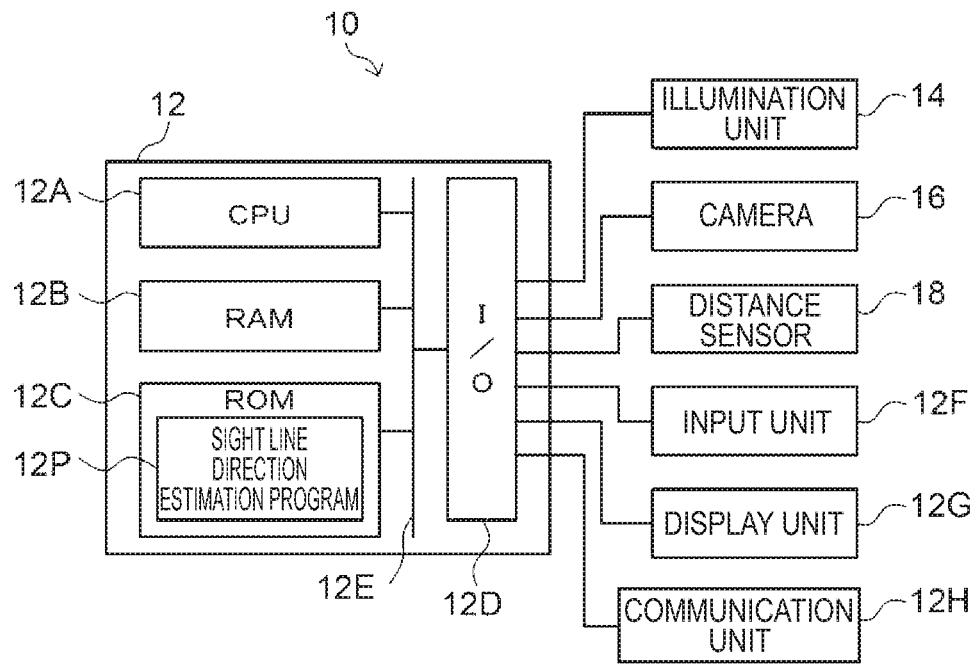
FIG. 1 is a block diagram illustrating an example of a configuration in which a sight line direction estimation device according to a first embodiment is realized by a computer.

FIG. 1 illustrates an example of a configuration in which a sight line direction estimation device 10 that operates as the sight line direction estimation device of the disclosed technique is realized by a computer.

As illustrated in FIG. 1, the computer that operates as the sight line direction estimation device 10 includes a device main body 12 including a Central Processing Unit (CPU) 12A, a Random Access Memory (RAM) 12B, and a Read Only Memory (ROM) 12C. The ROM 12C includes a sight line direction estimation program 12P for realizing various functions of estimating the sight line direction by suppressing a sight line error ρ. The device main body 12 includes an input/output interface (hereinafter, referred to as I/O) 12D, and the CPU 12A, the RAM 12B, the ROM 12C, and the I/O 12D are connected via a bus 12E so as to be able to exchange commands and data separately. An input unit 12F such as a keyboard and a mouse, a display unit 12G such as a display, and a communication unit 12H for communicating with an external device are connected to the I/O 12D. Further, an illumination unit 14 such as a near-infrared Light Emitting Diode (LED) that illuminates a head portion of an occupant, a camera 16 that captures an image the head portion of the occupant, and a distance sensor 18 that measures a distance to the head portion of the occupant are connected to the I/O 12D. Although not illustrated, a non-volatile memory capable of storing various data can be connected to the I/O 12D.

The device main body 12 operates as the sight line direction estimation device 10 by reading out the sight line direction estimation program 12P from the ROM 12C and developing the sight line direction estimation program 12P in the RAM 12B and executing the sight line direction estimation program 12P developed in the RAM 12B by the CPU 12A. The sight line direction estimation program 12P includes a process for realizing various functions of estimating the sight line direction by suppressing the sight line error ρ (details are described below).

In this embodiment, since it is possible to derive an actual sight line direction by a first derivation method (details are described below) of deriving the sight line direction using information related to a characteristic region that characteristically represents an eye, the illumination unit 14 is not an essential configuration, and can be omitted.

Figure 2:
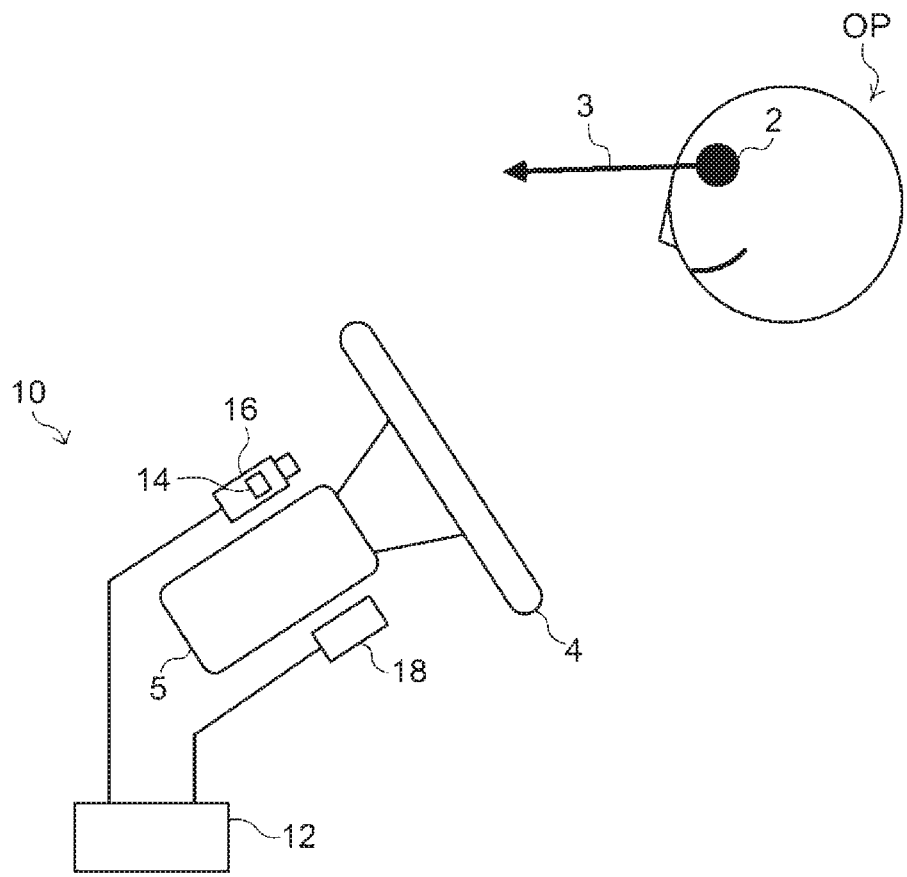
FIG. 2 is an image diagram illustrating an example of an arrangement of electronic equipment of the sight line direction estimation device according to the first embodiment.

FIG. 2 illustrates an example of an arrangement of electronic equipment mounted on a vehicle as the sight line direction estimation device 10.

As illustrated in FIG. 2, the vehicle is mounted with the device main body 12 of the sight line direction estimation device 10, the illumination unit 14 that illuminates an occupant, the camera 16 that captures an image of the head portion of an occupant OP, and the distance sensor 18. An arrangement example of this embodiment illustrates a case where the illumination unit 14 and the camera 16 are installed above a column 5 holding a steering 4, and the distance sensor 18 is installed below the column 5. In FIG. 2, the sight line direction of the occupant is illustrated as a sight line 3.

Figure 3:
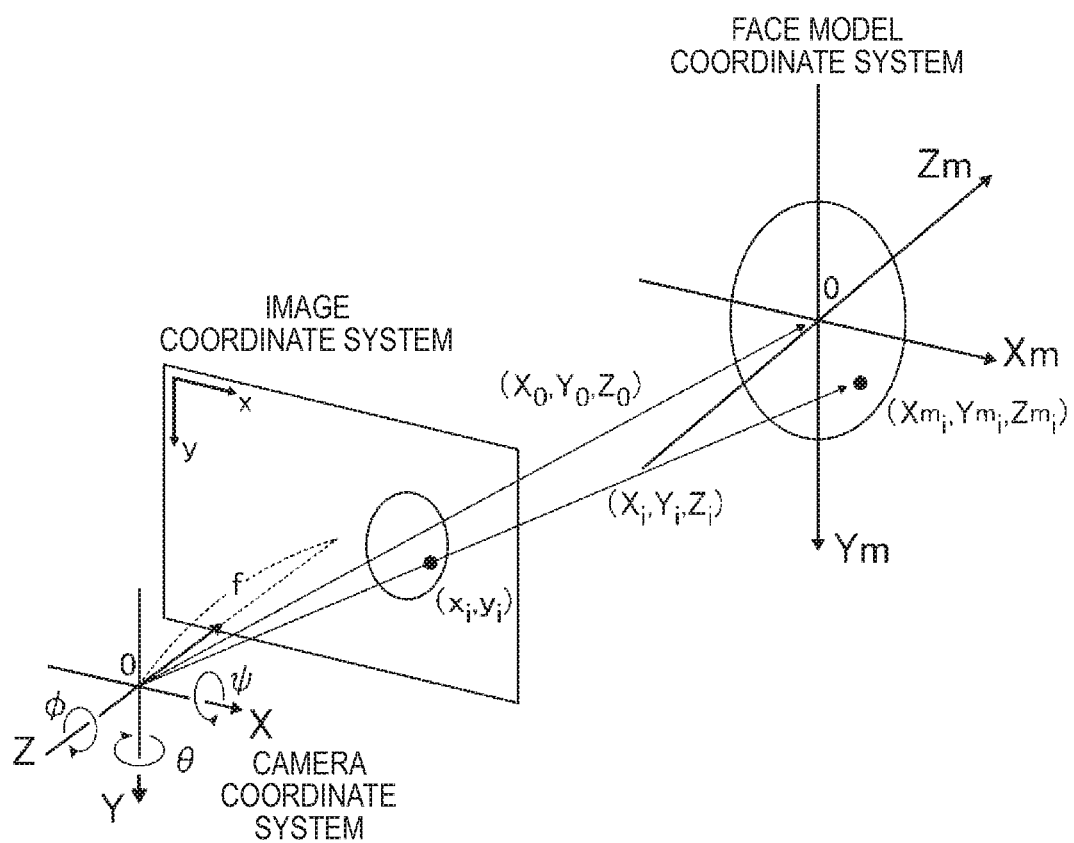
FIG. 3 is an image diagram illustrating an example of coordinate systems in the sight line direction estimation device according to the first embodiment.

FIG. 3 illustrates an example of coordinate systems in the sight line direction estimation device 10.

The coordinate systems in a case where a position is specified differ depending on how to handle an article as a center. Examples include a coordinate system centered on a camera that captures an image of a face of a person, a coordinate system centered on a captured image, and a coordinate system centered on the face of the person. In the following description, the coordinate system centered on the camera is referred to as a camera coordinate system, and the coordinate system centered on the face is referred to as a face model coordinate system. The example illustrated in FIG. 3 illustrates an example of a relationship between the camera coordinate system, the face model coordinate system, and an image coordinate system used in the sight line direction estimation device 10 according to this embodiment.

In the camera coordinate system, a right side is an X direction, a lower side is a Y direction, and a front side is a Z direction viewed from the camera 16, and an origin is derived by calibration. The camera coordinate system is determined such that directions of an x axis and a y axis coincide with those in the image coordinate system whose origin is the upper left of the image.

The face model coordinate system is for determining a position and posture of the face and expressing positions of regions of eyes and a mouth on the face. For example, face image processing generally uses a technique of projecting data onto an image using the data called a face model in which a three-dimensional position of a characteristic region of a face such as eyes and a mouth is described, and estimating the position and posture of the face by combining the positions of the eyes and the mouth. An example of the coordinate system set in the face model is the face model coordinate system, and a left direction is an Xm direction, a lower direction is a Ym direction, and a rear direction is a Zm direction viewed from the face.

A mutual relationship between the camera coordinate system, the face model coordinate system, and the image coordinate system is determined in advance, and coordinate conversion can be performed between the camera coordinate system, the face model coordinate system, and the image coordinate system. That is, since a distance between a head portion of the occupant OP and the camera 16 can be detected by the distance sensor 18 (see FIG. 2), the mutual relationship between the camera coordinate system, the face model coordinate system, and the image coordinate system can be specified using a camera performance such as a focal length of the camera 16 and the distance between the head portion and the camera 16. In the following description, a case where the camera coordinate system is applied will be described unless distinction is made.

Figure 4:
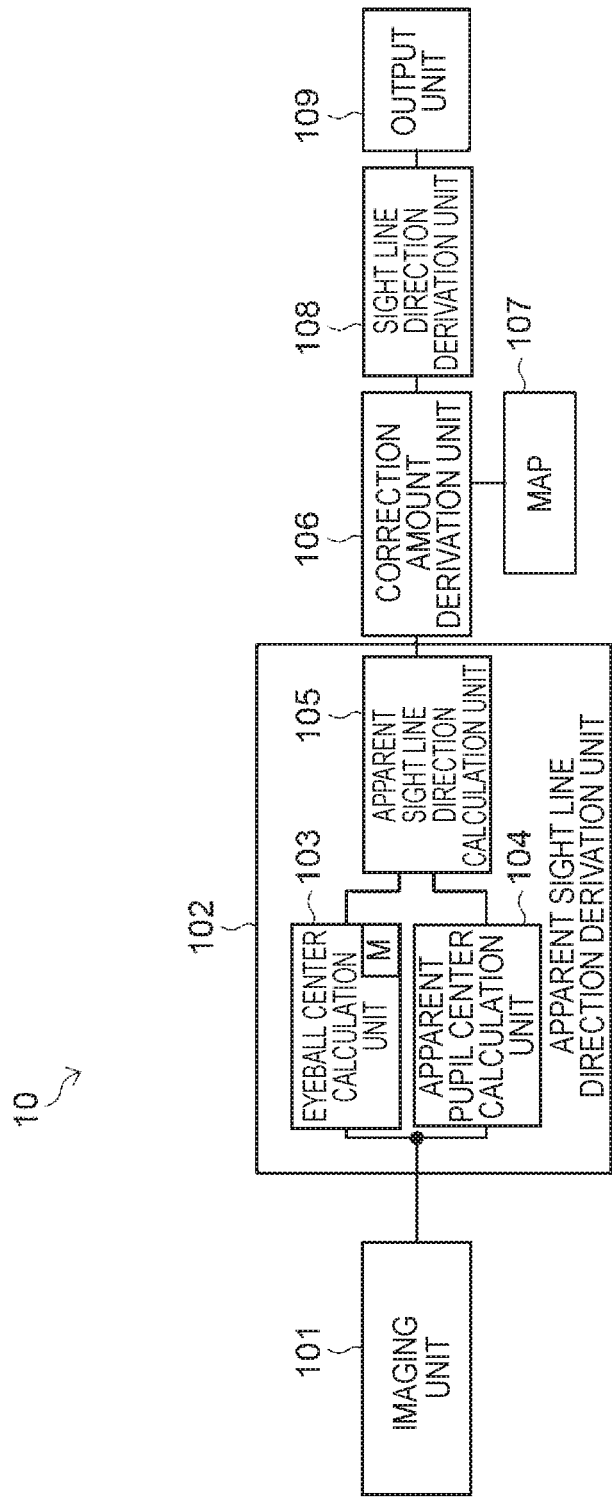
FIG. 4 is a block diagram illustrating an example of a configuration in which a device main body of the sight line direction estimation device according to the first embodiment is classified functionally.

FIG. 4 illustrates an example of a block configuration in which the device main body 12 of the sight line direction estimation device 10 according to this embodiment is classified in a functional configuration.

As illustrated in FIG. 4, the sight line direction estimation device 10 includes a imaging unit 101 such as a camera, an apparent sight line direction derivation unit 102, a correction amount derivation unit 106 to which a map 107 is connected, a sight line direction derivation unit 108, and an output unit 109.

The imaging unit 101 is a functional unit that acquires a captured image and outputs the captured image to the apparent sight line direction derivation unit 102. In this embodiment, the camera 16, which is an example of a imaging device, is used as an example of the imaging unit 101. The camera 16 captures the image of the head portion including a part of an eyeball of the occupant OP of the vehicle and outputs the captured image.

The apparent sight line direction derivation unit 102 is a functional unit that derives an apparent sight line direction, and derives the apparent sight line direction of the person using the captured image from the imaging unit 101. Here, the apparent sight line direction is derived from a three-dimensional eyeball center position and a three-dimensional pupil center position estimated from a two-dimensional captured image. That is, when the sight line direction of the person is specified, it is difficult to physically detect the eyeball center position and the pupil center position. Therefore, based on the two-dimensional captured image obtained by capturing at least the eyeball surface, the three-dimensional eyeball center position and the three-dimensional pupil center position are estimated, and a direction from the estimated eyeball center position to the pupil center position is derived as the apparent sight line direction.

The apparent sight line direction derivation unit 102 includes an eyeball center calculation unit 103, an apparent pupil center calculation unit 104, and an apparent sight line direction calculation unit 105 in order to derive the apparent sight line direction. The pupil of the eyeball included in the captured image is captured at the eyeball surface, that is, a position of light going through a cornea surface. The pupil center position observed on the cornea surface is described as an apparent pupil center position.

The eyeball center calculation unit 103 is a functional unit that calculates the eyeball center position based on the captured image, and performs a calculation of estimating the three-dimensional eyeball center position using the captured image from the imaging unit 101. The apparent pupil center calculation unit 104 is a functional unit that calculates the apparent pupil center position based on the captured image, and performs a calculation of estimating the three-dimensional apparent pupil center position using the captured image from the imaging unit 101. The apparent sight line direction calculation unit 105 is a functional unit that calculates the apparent sight line direction using the apparent eyeball center position and the apparent pupil center position. The apparent sight line direction calculation unit 105 calculates the apparent sight line direction using the eyeball center position calculated by the eyeball center calculation unit 103 and the apparent pupil center position calculated by the apparent pupil center calculation unit 104.

The correction amount derivation unit 106 is a functional unit that determines a correction amount from the apparent sight line direction to the actual sight line direction, and derives the correction amount using a corresponding relationship between the apparent sight line direction stored in the map 107 and the correction amount to the actual sight line direction. In the map 107, an error in the actual sight line direction of a person with respect to the apparent sight line direction is determined in advance as the correction amount, and a map in which the apparent sight line direction corresponds to the correction amount is memorized (details are described below).

The sight line direction derivation unit 108 is a functional unit that derives the actual sight line direction, and performs processing of deriving the sight line direction of the person by performing a calculation of correcting the apparent sight line direction calculated by the apparent sight line direction derivation unit 102 with the correction amount derived by the correction amount derivation unit 106. The output unit 109 outputs information indicating the sight line direction of the person calculated by the sight line direction derivation unit 108.

Here, the derivation of the apparent sight line direction includes a first derivation method of deriving the sight line direction using information related to the characteristic region that characteristically represents an eye, and a second derivation method by a so-called cornea reflection method of deriving the sight line direction using information related to the cornea. In the first derivation method, a two-dimensional position (a position on an image) of the characteristic region that characteristically represents an eye is detected, and an eyeball 2 modeled with a three-dimensional model is fitted based on the characteristic region, so that the eyeball center position is derived in three dimensions, and a three-dimensional sight line direction is derived. In the second derivation method, the three-dimensional sight line direction is derived using a position of reflected light of the cornea surface of light radiated toward the eyeball and a two-dimensional position (a position on the image) of the pupil center position.

Figure 5A:
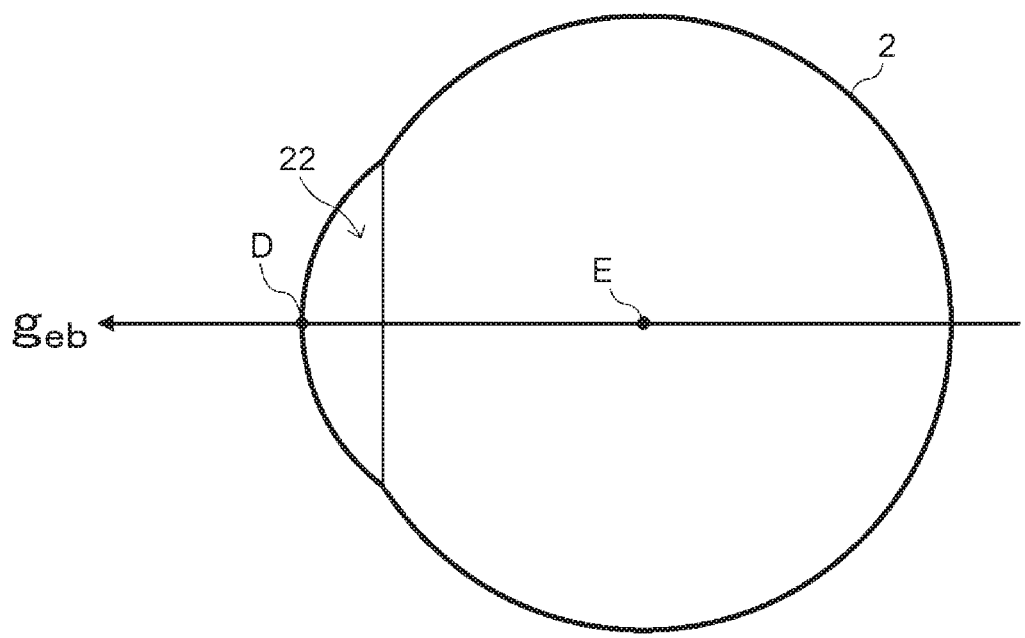
Figure 5B:
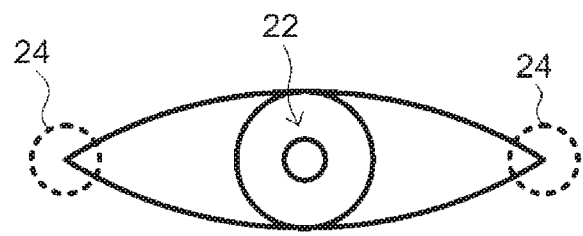

FIGS. 5A and 5B illustrate an example of a schematic diagram for explaining the first derivation method. FIG. 5A illustrates a sight line in the modeled eyeball 2, and FIG. 5B illustrates an example of an image obtained by capturing an eye on a face of a person.

As illustrated in FIG. 5B, the image obtained by capturing the eye includes a pupil 22 and characteristic regions 24 of an outer canthus and an inner canthus that characteristically represent the eye. In the first derivation method, an apparent pupil center position D observed on the cornea surface is calculated using the captured image. Then, a position of each characteristic region 24 as a characteristic point is calculated, and a three-dimensional eyeball model having a predetermined standard is fitted to the characteristic points of the outer canthus and the inner canthus. As illustrated in FIG. 5A, a center position of the fitted three-dimensional eyeball model is estimated as a center position E of the eyeball 2, and a vector connecting the center position E of the eyeball 2 and the apparent pupil center position D is taken as a sight line vector $g_{eb}$, that is, the apparent sight line direction.

Figure 6A:
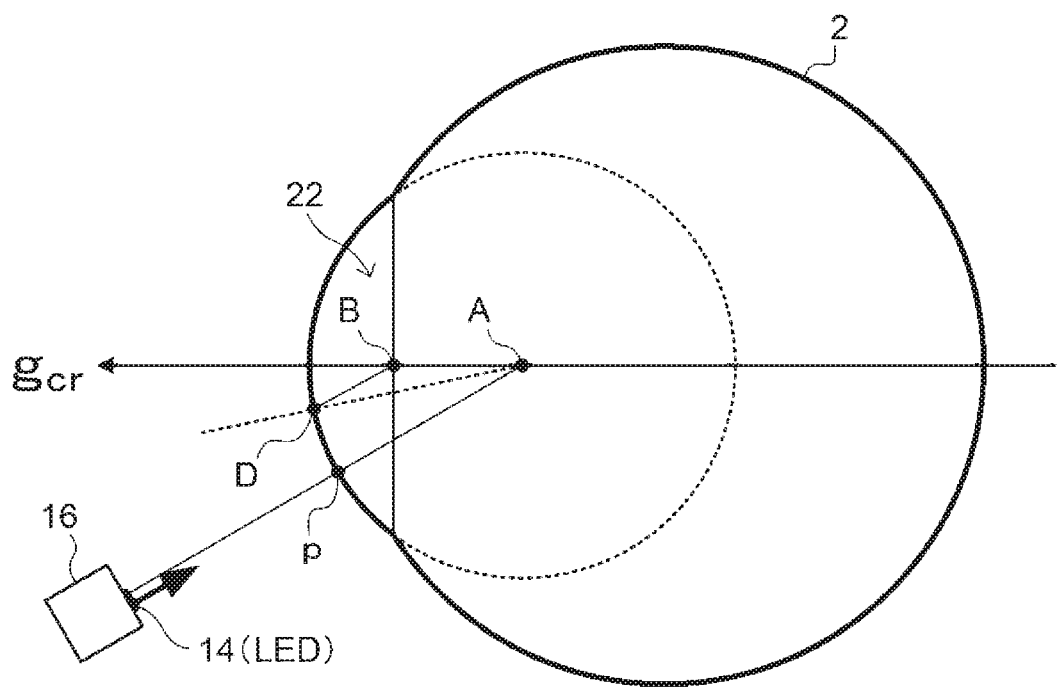
Figure 6B:
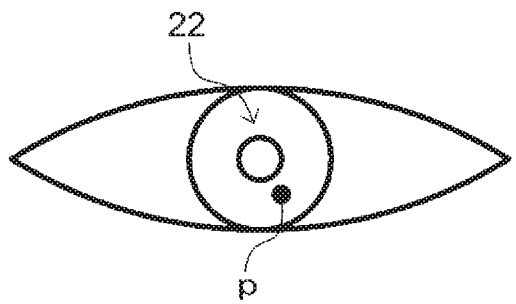

FIG. 6 illustrates an example of a schematic diagram for explaining the second derivation method. FIG. 6A illustrates a sight line in the modeled eyeball 2, and FIG. 6B illustrates an example of an image obtained by capturing an eye on a face of a person.

As illustrated in FIG. 6A, the camera 16 captures reflected light of near-infrared light radiated from the illumination unit 14 such as an LED disposed in the vicinity of the camera 16 that captures the eye of the person. In the camera 16, a reflected image in the cornea is captured in a position p of an intersection of the cornea and a straight line connecting a position A of a curvature center of the cornea and the illumination unit 14. That is, as illustrated in FIG. 6B, the reflected image in the cornea is formed around the pupil 22 (a position in a lower right direction of the pupil 22 in an example illustrated in FIG. 6B) in the captured image. In the second derivation method, based on a relationship between the cornea reflected image reflected on the cornea as the position p and the center position D of the pupil 22, a vector from the position A of the curvature center of the cornea to a center position B of the pupil determined from the apparent pupil center position D is estimated by a well-known method as a sight line vector $g_{cr}$.

Since light is refracted at the cornea of the eyeball, refraction of light at the cornea influences derivation of the apparent sight line direction. For example, the apparent sight line direction derived by the above first derivation method and the apparent sight line direction derived by the second derivation method may have an angle difference (hereinafter, referred to as a sight line error). The sight line error in the apparent sight line direction is described.

Figure 7:
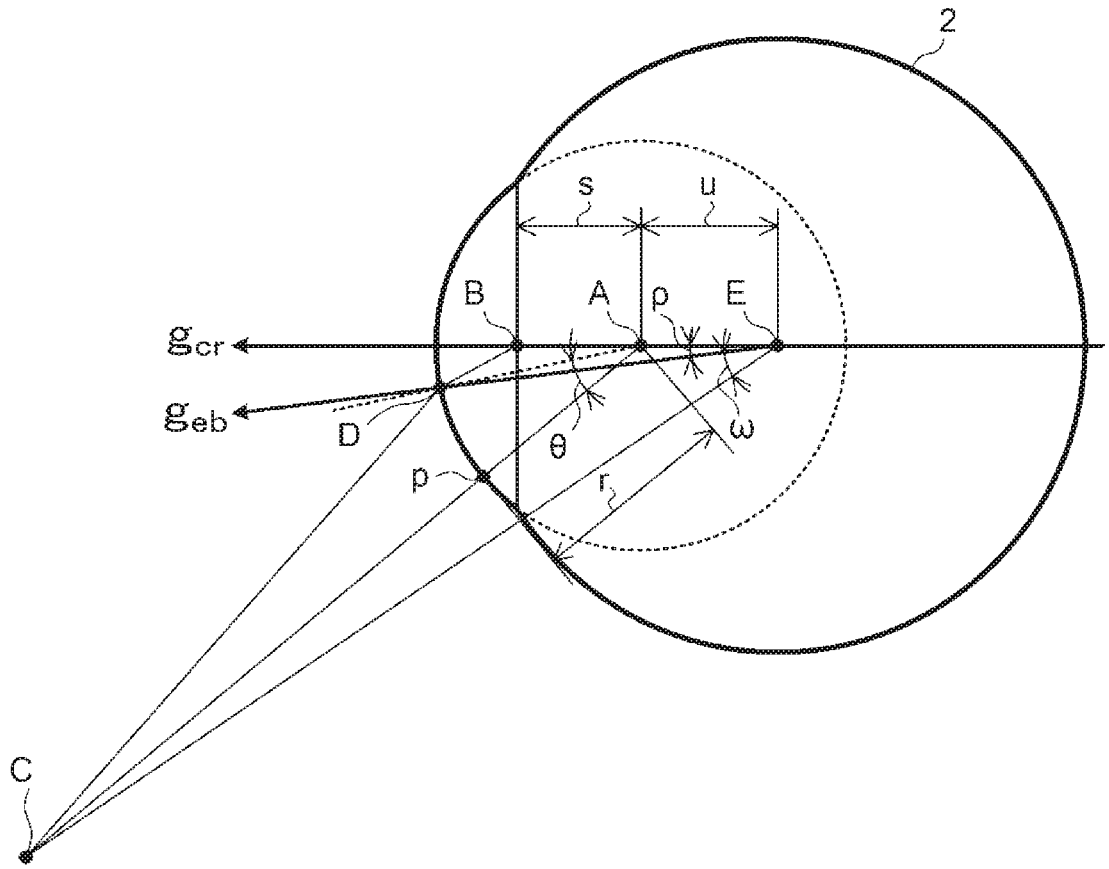
FIG. 7 is an image diagram illustrating an example of a detailed schematic diagram related to the sight line of the modeled eyeball.

FIG. 7 illustrates an example of a detailed schematic diagram related to the sight line of the modeled eyeball 2.

In FIG. 7, the center position A of the curvature of the cornea, the center position B of the pupil, and the center position E of the eyeball are illustrated as actual positions of the modeled eyeball 2. The position p of the reflected image by illumination on the cornea surface and the apparent pupil center position D observed on the cornea surface are illustrated as apparent positions. A position C is a position of an imaging device of the camera. In FIG. 7, the positions are illustrated by a distance s between the position A and the position B, a distance u between the position A and the position E, and a distance r between the position A and the position p. Further, the positions are illustrated by an angle θ formed between a vector from the position A to the position D and a vector from the position A to the position p, an angle (sight line error) ρ formed between a vector from the position E to the position B and a vector from the position E to the position D, and an angle ω formed between the vector from the position E to the position D and a vector from the position E to the position C.

In the second derivation method, since the position A of the curvature center of the cornea can be derived using a cornea reflection method, information on the position p of the cornea reflected image, the position A of the curvature center of the cornea, and the apparent pupil center position D observed on the cornea surface can be obtained as information related to the cornea. The center position E of the eyeball 2 can also be derived using information related to the cornea. Accordingly, the calculation is possible in consideration of the refraction of light at the cornea, and the sight line vector $g_{cr}$ from the center position E of the eyeball 2 to the center position B of the pupil can be derived.

On the other hand, in the first derivation method, since the observed position is fitted to the modeled eyeball 2, the information related to the cornea is only the apparent pupil center position D, and the refraction of light at the cornea cannot be considered. That is, in the first derivation method, a vector connecting the apparent pupil center position and the eyeball center position is calculated as the sight line vector. Therefore, the sight line vector $g_{cr}$ calculated by the second derivation method may not coincide with the sight line vector $g_{eb}$ calculated by the first derivation method. The angle ρ of an angle difference between the sight line vector $g_{cr}$ and the sight line vector $g_{eb}$, which is the sight line error, is not constant, but varies depending on the position and orientation of the eyeball 2. Therefore, a degree of deterioration of estimation accuracy of the sight line direction derived by the first derivation method increases as the sight line error ρ increases with respect to the sight line vector $g_{cr}$ calculated by the second derivation method.

Here, assuming that the sight line vector $g_{cr}$ is approximate to the actual sight line vector, in a case where the actual sight line vector is toward the position C of the imaging device of the camera, the actual sight line vector substantially coincides with the sight line vector $g_{eb}$. On the other hand, the sight line error ρ increases as the angle from the actual sight line vector toward the position C of the imaging device of the camera increases. This means that the sight line error p increases as the sight line direction deviates from a direction toward the camera, and the sight line error ρ has a correlation with the angle ω formed between the sight line vector $g_{eb}$ and the vector from the center position E of the eyeball 2 to the position C of the imaging device of the camera.

Therefore, if the correlation between the sight line error ρ and the angle ω is known, the actual sight line vector can be derived from the apparent sight line vector $g_{eb}$.

Figure 8:
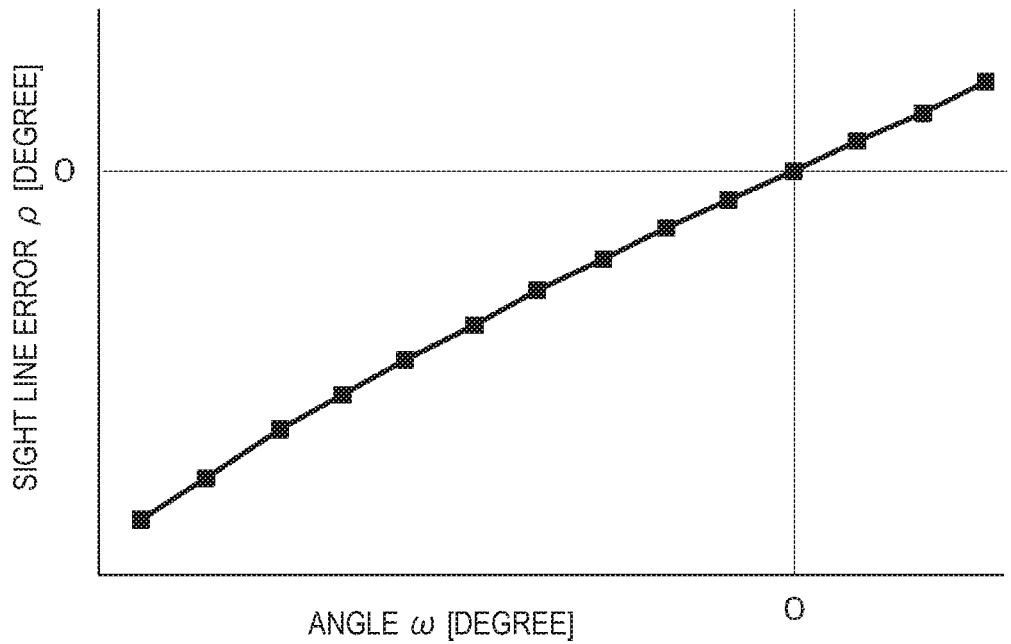
FIG. 8 is an image diagram illustrating an example of a map illustrating a corresponding relationship between a sight line error and an angle with respect to a direction toward a camera.

FIG. 8 illustrates an example of the correlation between the sight line error ρ and the angle ω.

FIG. 8 is derived by an experiment of the correlation between the angle ω and the sight line error ρ that occurs when the sight line direction of a person is actually changed. As illustrated in FIG. 8, when the sight line direction of the person is toward the camera, the sight line error ρ and the angle ω are zero because the actual sight line vector substantially coincides with the sight line vector $g_{eb}$. Further, the sight line error ρ (absolute value) increases as the sight line deviates from the direction toward the camera.

Therefore, the sight line direction estimation device 10 according to this embodiment estimates the sight line direction by suppressing the sight line error ρ. That is, in this embodiment, the correlation illustrated in FIG. 8 is used as the correction amount, that is, in the sight line direction estimation device 10, an error in the actual sight line direction of the person with respect to the apparent sight line direction is determined in advance as the correction amount, and is memorized in the map 107 by corresponding the apparent sight line direction and the correction amount. Therefore, the correction amount derivation unit 106 derives the correction amount memorized in the map 107 as the error in the actual sight line direction of the person with respect to the apparent sight line direction using the apparent sight line direction derived by the apparent sight line direction derivation unit 102. Then, the sight line direction derivation unit 108 can derive the actual sight line direction (sight line vector) using the correction amount derived by the correction amount derivation unit 106.

Next, an operation of the sight line direction estimation device 10 that estimates the sight line direction by suppressing the sight line error ρ is described. In this embodiment, the sight line direction estimation device 10 is operated by the device main body 12 of the computer.

Figure 9:
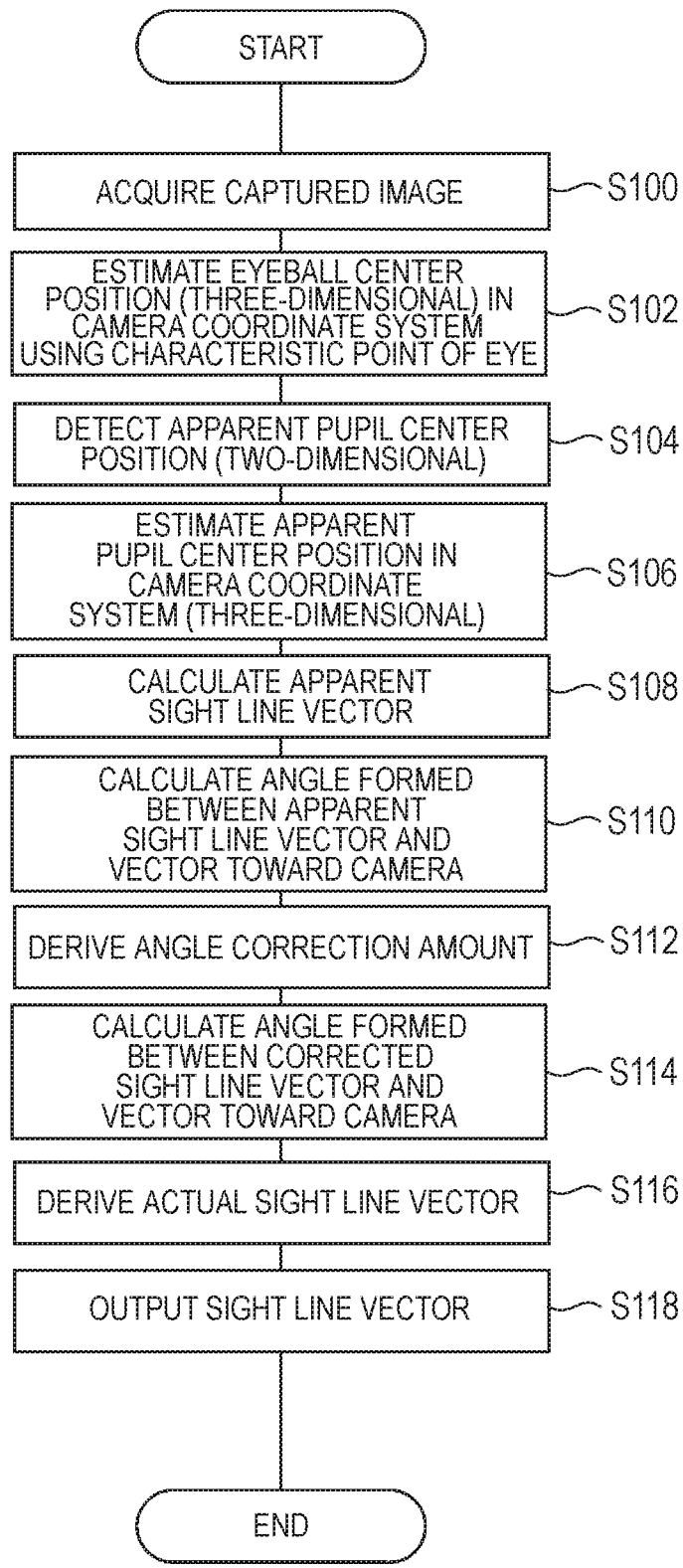
FIG. 9 is a flowchart illustrating an example of a flow of processing of the sight line direction estimation device by the computer according to the first embodiment.

FIG. 9 illustrates an example of a flow of processing by the sight line direction estimation program 12P in the sight line direction estimation device 10 realized by the computer. In the device main body 12, the sight line direction estimation program 12P is read out from the ROM 12C and developed in the RAM 12B, and the sight line direction estimation program 12P developed in the RAM 12B is executed by the CPU 12A.

First, in step S100, processing of acquiring the image captured by the camera 16 is performed. Processing of step S100 is an example of an operation of acquiring the captured image output from the imaging unit 101 illustrated in FIG. 4.

In next step S102, the three-dimensional center position E of the eyeball 2 in the camera coordinate system is estimated using the characteristic point of the eye such as the inner canthus and the outer canthus on the captured image. Processing of step S102 is an example of an operation of the eyeball center calculation unit 103 included in the apparent sight line direction derivation unit 102 illustrated in FIG. 4. In step S102, the center position of the eyeball 2 is derived using the first derivation method described above to estimate the three-dimensional center position of the eyeball 2. First, the captured image is processed, and face characteristic positions indicating the regions of the eye and the mouth in the face model coordinate system are specified, so that the position and posture of the face are estimated. Next, the characteristic point of the eye such as the inner canthus and the outer canthus is specified, and the eyeball 2 modeled by the three-dimensional model is fitted to the estimated position and posture of the face and the eye characteristic point, so that the center position of the eyeball 2 is derived in three dimensions. Coordinates $e=(e_x, e_y, e_z)^t$ of the center position E of the eyeball 2 are determined by converting the center position of the eyeball 2 of the derived face model coordinate system into the center position of the eyeball 2 of the camera coordinate system.

Next, in step S104, the captured image is processed to detect the apparent pupil center position D on the captured image. Here, center coordinates detected as the two-dimensional position of the image coordinate system on the captured image in step S104 are $D=(D_x, D_y)$.

In next step S106, the three-dimensional apparent pupil center position D in the camera coordinate system is estimated based on the apparent pupil center position D in the image coordinate system. First, a Z coordinate of the apparent pupil center position D in the camera coordinate system is $d_z$ using a distance measurement result detected by the distance sensor 18. Here, three-dimensional coordinates $d=(D_x, D_y, D_z)$ of the apparent pupil center position D in the camera coordinate system can be expressed by the following formula (1) when a focal length f of the camera 16 is a focal length expressed in a pixel unit. The three-dimensional apparent pupil center position D is estimated using the formula (1).

$$d=((D_x d_z)/f, (D_y d_z)/f, d_z) \tag{1}$$

Processing of step S104 and step S106 is an example of an operation of the apparent pupil center calculation unit 104 included in the apparent sight line direction derivation unit 102 illustrated in FIG. 4.

Next, in step S108, the apparent sight line vector is calculated using the center position E of the eyeball 2 estimated in step S102 and the apparent pupil center position D estimated in step S106. The apparent sight line vector is a vector connecting the center position E of the eyeball 2 and the apparent pupil center position D. When the vector is an apparent sight line vector $g_{eb}=(g_{eb\_x}, g_{eb\_y}, g_{eb\_z})$, the apparent sight line vector $g_{eb}$ can be expressed by the following formula (2).

$$g_{eb} = d - e = \begin{pmatrix} \frac{D_x d_z}{f} - e_x \\ \frac{D_y d_z}{f} - e_y \\ d_z - e_z \end{pmatrix} \tag{2}$$

Processing of step S108 is an example of an operation of the apparent sight line direction calculation unit 105 included in the apparent sight line direction derivation unit 102 illustrated in FIG. 4.

In next step S110, the angle ω formed between the apparent sight line vector $g_{eb}$ and the vector from the center position E of the eyeball 2 to the position C of the imaging device of the camera is derived.

That is, the sight line vector connecting the center position E of the eyeball 2 estimated by step S102 and the apparent pupil center position D estimated by step S106 is the apparent sight line vector $g_{eb}=(g_{eb\_x}, g_{eb\_y}, g_{eb\_z})$. Since the position C is an origin of the camera coordinate system, the vector connecting the position E and the position C is a vector EC $(=(-e)=(-e_x, -e_y, -e_z)^t)$, and the angle ω of an inner product of the vector can be expressed by the following formula (3).

$$\omega = \cos^{-1}\left(\frac{g_{eb} \cdot (-e)}{\|g_{eb}\| \|-e\|}\right) = \cos^{-1}\left(\frac{-g_{eb} \cdot e}{\|g_{eb}\| \|e\|}\right) \tag{3}$$

When the formula (2) is substituted into the formula (3), a result is expressed by the following formula (4), and the angle ω can be determined.

$$\omega = \tag{4}$$

$$\cos^{-1}\left(\frac{-\left(\frac{D_x d_z}{f} - e_x\right)e_x - \left(\frac{D_y d_z}{f} - e_y\right)e_y - (d_z - e_z)e_z}{\sqrt{\left(\frac{D_x d_z}{f} - e_x\right)^2 + \left(\frac{D_y d_z}{f} - e_y\right)^2 + (d_z - e_z)^2} \sqrt{e_x^2 + e_y^2 + e_z^2}}\right)$$

In this case, since a sign (positive/negative) of the angle ω cannot be specified in the formula (4), positive/negative of the angle ω is set to be positive if $-((D_y d_z)/f)e_z + d_z e_y$, which is an x component of a cross product $g_{eb} \times (-e)$ shown in the following formula (5) is positive, and to be negative if $-((D_y d_z)/f)e_z + d_z e_y$ is negative.

$$g_{eb} \times (-e) = \tag{5}$$

-continued $$\begin{pmatrix} -\left(\frac{D_y d_z}{f} - e_y\right)e_z + (d_z - e_z)e_y \\ -(d_z - e_z)e_x + \left(\frac{D_x d_z}{f} - e_x\right)e_z \\ -\left(\frac{D_x d_z}{f} - e_x\right)e_y + \left(\frac{D_y d_z}{f} - e_y\right)e_x \end{pmatrix} = \begin{pmatrix} -\left(\frac{D_y d_z}{f}\right)e_z + d_z e_y \\ -d_z e_x + \left(\frac{D_x d_z}{f}\right)e_z \\ -\left(\frac{D_x d_z}{f}\right)e_y + \left(\frac{D_y d_z}{f}\right)e_x \end{pmatrix}$$

Next, in step S112, the sight line error ρ corresponding to the angle ω derived in step S110 is extracted, and an angle correction amount is derived with reference to the map 107. Processing of step S110 and step S112 is an example of an operation of the correction amount derivation unit 106 illustrated in FIG. 4.

Then, in a next step S114, an angle formed between the corrected sight line vector and the vector toward the camera is calculated. Next, in step S116, the actual sight line direction (sight line vector) in the camera coordinate system is derived using an apparent sight line vector calculated in step S108, an angle calculated in step S110, and an angle calculated in step S114. Then, in next step S118, the actual sight line direction (sight line vector) in the camera coordinate system derived in step S116 is output, and this processing routine is ended.

Processing of step S114 and step S116 is an example of an operation of the sight line direction derivation unit 108 illustrated in FIG. 4. Processing of step S118 is an example of an operation of the output unit 109 illustrated in FIG. 4.

An example of processing of deriving the actual sight line direction (sight line vector) in the camera coordinate system in the above step S116 is described.

First, an actual angle estimated by the processing of step S110 and step S112 is ω+ρ. The actual sight line vector is derived using the actual angle (ω+ρ) estimated by the processing of step S110 and step S112 and an angle of the apparent sight line vector calculated in step S108. Here, the actual sight line vector is denoted as $g'_{eb} = (g'_{eb\_x}, g'_{eb\_y}, g'_{eb\_z})$. $g'_{eb}$ is determined by the following calculation.

In this embodiment, a case where a formula is derived using Rodrigues's rotation formula is described as an example.

In the Rodrigues's rotation formula, when a vector obtained by rotating a three-dimensional vector v by an angle θ around a three-dimensional unit vector k as a rotation axis is $v_{rot}$, the vector $v_{rot}$ is given by the following formula (6). Here, the angle θ is determined by a right-handed system.

$$v_{rot} = v \cos\theta + (k \times v)\sin\theta + k(k \cdot v)(1 - \cos\theta) \qquad (6)$$

Since the actual sight line vector $g'_{eb}$ is obtained by rotating the vector $g_{eb}$ by an angle ρ on a plane including the vector $g_{eb}$ and the vector EC, in the formula (6), $v = g_{eb}$, $v_{rot} = g'_{eb}$, θ=ρ, and the rotation axis k is a normal vector of the plane including the vector $g_{eb}$ and the vector EC. k is determined by the following formula (7) by a cross product (k is a unit vector).

$$k = \frac{g_{eb} \times \overrightarrow{EC}}{\|g_{eb} \times \overrightarrow{EC}\|} = \frac{g_{eb} \times (-e)}{\|g_{eb} \times (-e)\|} = \frac{-g_{eb} \times e}{\|g_{eb} \times e\|} = \frac{-g_{eb} \times e}{\|g_{eb}\| \|e\| |\sin\omega|} \qquad (7)$$

By substituting these v, $v_{rot}$, θ, and k into the formula (6) and making transformation, the following formula (8) is obtained.

$$g'_{eb} = g_{eb}\cos\rho + \left(\left(\frac{-g_{eb} \times e}{\|g_{eb}\| \|e\| |\sin\omega|}\right) \times g_{eb}\right)\sin\rho + \qquad (8)$$
$$\left(\frac{-g_{eb} \times e}{\|g_{eb}\| \|e\| |\sin\omega|}\right)\left(\left(\frac{-g_{eb} \times e}{\|g_{eb}\| \|e\| |\sin\omega|}\right) \cdot g_{eb}\right)(1 - \cos\rho) =$$
$$g_{eb}\cos\rho - \frac{((g_{eb} \times e) \times g_{eb})\sin\rho}{\|g_{eb}\| \|e\| |\sin\omega|} + \frac{(g_{eb} \times e)((g_{eb} \times e) \cdot g_{eb})(1 - \cos\rho)}{(\|g_{eb}\| \|e\| |\sin\omega|)^2}$$

In this manner, the actual sight line vector $g'_{eb}$ can be determined from the vector $g_{eb}$, the angle ω, and the angle ρ.

As described above, according to the sight line direction estimation device of this embodiment, the apparent sight line direction derived without considering refraction of light at the cornea of the eyeball is corrected in the actual sight line direction. That is, the sight line direction is derived so as to suppress a sight line error between the derived apparent sight line direction and the actual sight line direction. Accordingly, even when the sight line direction is derived without considering the refraction of light at the cornea of the eyeball, it is possible to derive the sight line direction with high accuracy in the actual sight line direction.

Although an example in which a corresponding relationship between the angle ω and the sight line error ρ is memorized in the map 107 and the actual sight line vector is derived with reference to the map 107 is described in this embodiment, the disclosed technique does not limit the corresponding relationship memorized in the map 107 to the angle ω and the sight line error ρ. For example, instead of the angle ω, a vector related to the angle ω may be memorized as a parameter, and the sight line error ρ may correspond to the memorized parameter and memorized in the map 107. An example of a vector related to the angle ω includes the apparent sight line vector $g_{eb}$ and the vector EC from the center position of the eyeball 2 to the camera 16.

Second Embodiment

Next, a second embodiment will be described. Regarding derivation of a sight line direction, the second embodiment applies a technique disclosed in a sight line direction estimation device capable of switching between the derivation of the sight line direction by the first derivation method and the derivation of the sight line direction by the second derivation method. Since the second embodiment has a configuration substantially the same as that of the first embodiment, the same parts are denoted by the same reference numerals, and a detailed description thereof is omitted.

In this embodiment, since a three-dimensional sight line direction is derived using a position of reflected light on a cornea surface of light radiated toward an eyeball (second derivation method), the illumination unit 14 is an essential component.

In the derivation of the sight line direction, using the position of the reflected light on the cornea surface, the three-dimensional sight line direction can be derived with high accuracy. However, it is difficult to always detect the position of the reflected light on the cornea surface, that is, it may be difficult to always detect the position of the reflected light by a cornea reflection method. Therefore, in this embodiment, when it is difficult to derive the sight line direction by the second derivation method, the sight line direction is derived by the first derivation method.

Figure 10:
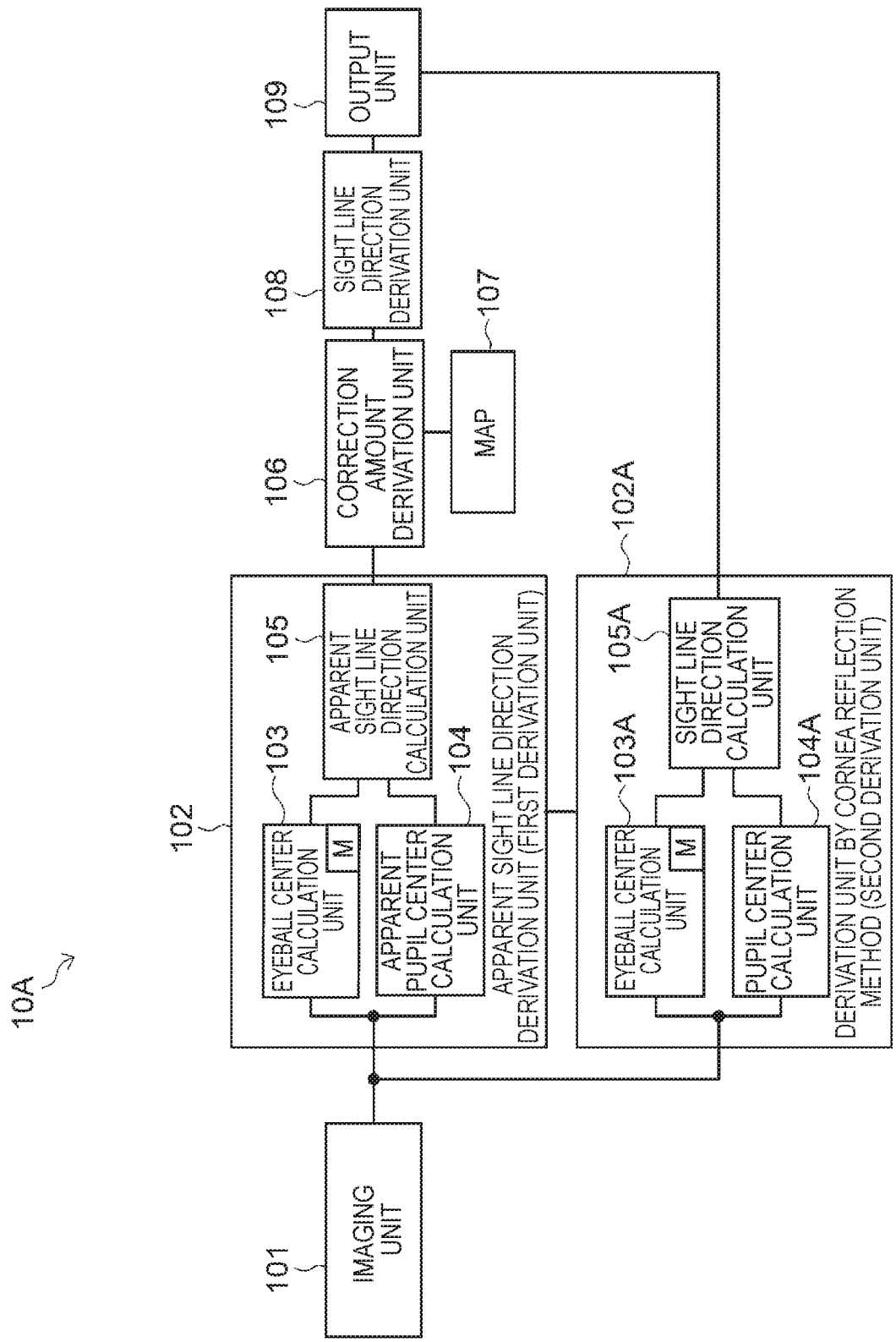
FIG. 10 is a block diagram illustrating an example of a configuration in which a device main body of a sight line direction estimation device according to a second embodiment is classified functionally.

FIG. 10 illustrates an example of a block configuration in which the device main body 12 of the sight line direction estimation device 10A according to this embodiment is classified in a functional configuration.

As illustrated in FIG. 10, the sight line direction estimation device 10A further includes a derivation unit 102A by the cornea reflection method in the sight line direction estimation device 10 illustrated in FIG. 4. In the following description, the apparent sight line direction derivation unit 102 illustrated in FIG. 4 is referred to as a first derivation unit 102, and the derivation unit 102A by the cornea reflection method is referred to as a second derivation unit 102A.

The second derivation unit 102A included in the sight line direction estimation device 10A of this embodiment includes an eyeball center calculation unit 103A, a pupil center calculation unit 104A, and a sight line direction calculation unit 105A. The sight line direction derivation unit 102A is a functional unit that derives the sight line direction by the cornea reflection method, and derives the sight line direction of a person in consideration of refraction of light at the cornea surface using a captured image from the imaging unit 101.

The eyeball center calculation unit 103A is a functional unit that calculates the eyeball center position based on the captured image, and performs a calculation of estimating the three-dimensional eyeball center position using the captured image from the imaging unit 101. The pupil center calculation unit 104A is a functional unit that calculates the pupil center position of a pupil based on the captured image and performs a calculation of estimating the three-dimensional apparent pupil center position using the captured image from the imaging unit 101. The sight line direction calculation unit 105A is a functional unit that calculates the sight line direction using the eyeball center position and the apparent pupil center position. The apparent sight line direction calculation unit 105A calculates the sight line direction of the person in consideration of the refraction of light at the cornea surface using the eyeball center position calculated by the eyeball center calculation unit 103A and the pupil center position calculated by the pupil center calculation unit 104A.

Since the sight line direction of the person that takes the refraction of light at the cornea surface into consideration and is derived by the second derivation unit 102A substantially coincides with the actual sight line direction, the sight line of the person is output to the output unit 109, and information indicating the sight line direction of the person is output from the output unit 109.

In this embodiment, each of the eyeball center calculation unit 103 of the first derivation unit 102 and the eyeball center calculation unit 103A of the second derivation unit 102A includes a memory (denoted as a symbol M in FIG. 10) that memorizes information indicating the center position of the eyeball 2.

Next, an operation of estimating the sight line direction by suppressing the sight line error ρ in the sight line direction estimation device 10A according to this embodiment will be described. In this embodiment, the sight line direction estimation device 10A is operated by the device main body 12 of the computer.

Figure 11:
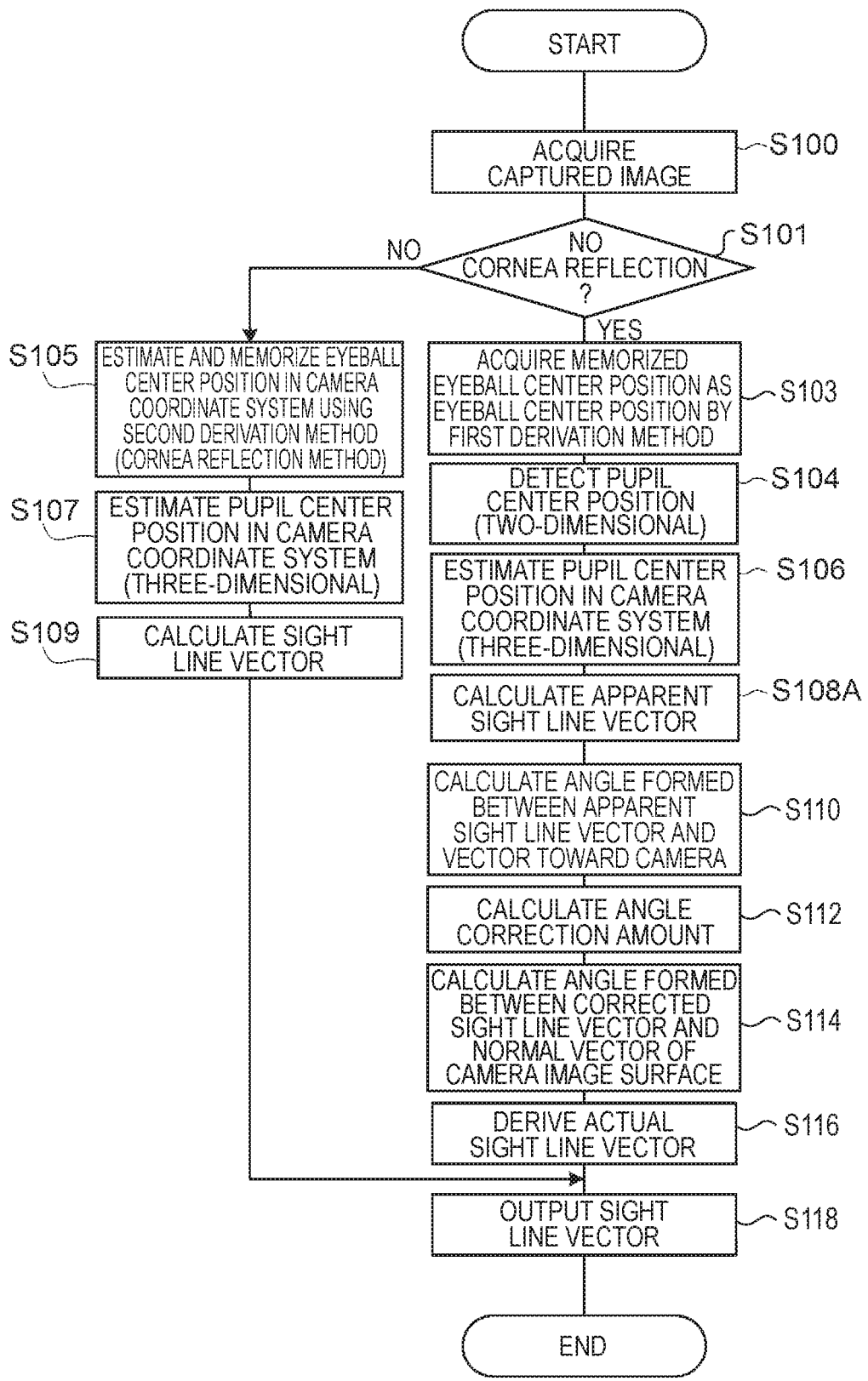
FIG. 11 is a flowchart illustrating an example of a flow of processing of the sight line direction estimation device by the computer according to the second embodiment.

FIG. 11 illustrates an example of a flow of processing by the sight line direction estimation program 12P in the sight line direction estimation device 10A realized by the computer.

In the device main body 12, the sight line direction estimation program 12P is read out from the ROM 12C and developed in the RAM 12B, and the sight line direction estimation program 12P developed in the RAM 12B is executed by the CPU 12A. The flow of the processing illustrated in FIG. 11 performs processing of steps S101, S103, S105, S107, and S109 instead of the processing of step S102 illustrated in FIG. 9. Processing of step S108A is performed instead of the processing of step S108 illustrated in FIG. 9.

In this embodiment, when the image captured by the camera 16 is acquired in step S100, whether cornea reflection occurs is determined by determining whether the reflected image of light radiated from the illumination unit 14 is included in the captured image in step S101. Processing of step S101 is an example of processing of determining whether the derivation processing of the sight line direction by the second derivation unit is possible.

That is, when positive determination is made in step S101, the processing proceeds to step S103 in order to derive an apparent sight line direction by the first derivation unit 102. On the other hand, when negative determination is made in step S101, the processing proceeds to step S105 in order to derive the sight line direction by the second derivation unit 102A.

In step S105, the three-dimensional center position E of the eyeball 2 in a camera coordinate system is estimated using the second derivation method by the cornea reflection method. The processing of step S103 is an example of the operation of the eyeball center calculation unit 103A included in the sight line direction derivation unit 102A illustrated in FIG. 10.

As illustrated in FIG. 7, when a coordinate of the center position A of curvature of the cornea in the camera center coordinate system is $a=(a_x, a_y, a_z)^t$, the sight line vector determined by the second derivation method is $g_{cr}=(g_{cr\_x}, g_{cr\_y}, g_{cr\_z})^t$, and a distance between the center position A of the curvature of the cornea and the center position E of the eyeball 2 is u, the coordinate $e=(e_x, e_y, e_z)^t$ of the center position E of the eyeball 2 in the camera center coordinate system can be expressed by the following formula (9). A vector a and the sight line vector $g_{cr}$ can be determined by the cornea reflection method.

$$e = a - u \frac{g_{cr}}{\|g_{cr}\|} \qquad (9)$$

In step S105, the coordinate e of the center position E of the eyeball 2 in the derived camera center coordinate system is memorized in the memory. In step S105, the coordinate e of the center position E of the eyeball 2 is commonly memorized in the memory of each of the eyeball center calculation unit 103 of the first derivation unit 102 and the eyeball center calculation unit 103A of the second derivation unit 102A.

In the next step S107, the three-dimensional pupil center position B in the camera coordinate system is estimated using a well-known method by the second derivation method of the cornea reflection method. In the next step S109, the sight line vector $g_{cr}$ is derived using the center position E of the eyeball 2 estimated in step S105 and the center position B of the pupil estimated in step S107. That is, the sight line vector $g_{cr}$ is a vector connecting the center position E of the eyeball 2 and the pupil center position B. Then, the processing proceeds to step S118, and the sight line vector $g_{cr}$ is output.

Processing of step S105 is an example of an operation of the eyeball center calculation unit 103A illustrated in FIG. 10, and processing of step S107 is an example of an operation of the pupil center calculation unit 104A, and processing of step S109 is an example of an operation of the sight line direction calculation unit 105A.

On the other hand, when positive determination is made in step S101, the processing proceeds to step S103 in order to derive an apparent sight line direction by the first derivation unit 102. In step S103, the coordinate $e=(e_x, e_y, e_z)^t$ of the center position E of the eyeball 2 in the camera center coordinate system memorized in the memory is acquired. When the coordinate e of the center position E of the eyeball 2 is not memorized in step S105, the center position E of the eyeball 2 may be derived in the same manner as step S102 illustrated in FIG. 9.

Next, as described above, in step S104, the apparent pupil center position D (two-dimensional position) is detected, and in the next step S106, the three-dimensional apparent pupil center position D in the camera coordinate system is estimated.

Next, in step S108A, an apparent sight line vector is calculated. When the coordinate e of the center position E of the eyeball 2 is not memorized in step S105, the apparent sight line vector $g_{eb}$ is calculated using the center position E of the eyeball 2 estimated in the same manner as step S102 and the apparent pupil center position D estimated in step S106 (see the above formula (2)).

On the other hand, when the coordinate e of the center position E of the eyeball 2 is memorized in step S105, in step S108A, the apparent sight line vector $g_{eb}$ is calculated using the following formula (10) instead of the above formula (2).

$$g_{eb} = d - e = d - a + u\frac{g_{cr}}{\|g_{cr}\|} = \begin{pmatrix} \frac{D_x d_z}{f} - a_x + u\frac{g_{cr\_x}}{\|g_{cr}\|} \\ \frac{D_y d_z}{f} - a_y + u\frac{g_{cr\_y}}{\|g_{cr}\|} \\ d_z - a_z + u\frac{g_{cr\_z}}{\|g_{cr}\|} \end{pmatrix} \quad (10)$$

Then, as described above, in step S110, the angle $\omega$ is derived, and in step S112, the sight line error $\rho$ corresponding to the angle $\omega$ derived in step S110 is extracted, and an angle correction amount is derived with reference to the map 107. Next, in step S114, an angle formed between a corrected sight line vector and a vector toward the camera is calculated, and in step S116, an actual sight line direction (sight line vector) in the camera coordinate system is derived. Then, in step S118, the actual sight line direction (sight line vector) in the camera coordinate system is output, and this processing routine is ended.

As described above, according to the sight line direction estimation device of this embodiment, the sight line direction is derived so as to suppress the sight line error even when the derivation of the sight line direction considering the refraction of light at the cornea is switched to the derivation of the sight line direction without considering the refraction of light at the cornea. Accordingly, even when the sight line direction is derived without considering the refraction of light at the cornea of the eyeball, it is possible to derive the sight line direction with high accuracy in the actual sight line direction.

In addition, since the center position of the eyeball 2 when the sight line direction is derived considering the refraction of light at the cornea is memorized and used when the sight line direction is derived, the actual sight line direction can be derived with high accuracy, as compared with a case where the eyeball center position is derived using only the characteristic point of the eye on the captured image.

The device body 12 included in the sight line direction estimation device according to each of the above embodiments may construct each constituent element by a hardware such as an electronic circuit having the functions described above, and may construct at least a part of constituent elements so as to realize the function by the computer.

In addition, in each of the above embodiments, in order to simplify the description, a case where the sight line direction is derived for one eyeball 2 is described, but the sight line direction may be derived for each of a plurality of eyeballs 2. In this case, it is preferable to specify one direction viewed by the pair of left and right eyeballs 2. At least one eyeball 2 of the pair of left and right eyeballs 2 may be an estimation target in the sight line direction. In this case, among the pair of left and right eyeballs 2, the eyeball 2 capable of deriving the sight line direction by the second derivation method may be selected as the target, or the eyeball 2 on a high-definition captured image may be selected as the target by comparing an image obtained by capturing the pair of left and right eyeballs 2.

Further, in each of the above embodiments, an example in which a corresponding relationship between the angle $\omega$ and the sight line error $\rho$ is memorized in the map 107 in advance is described in order to simplify the description, but the disclosed technique is not limited to memorizing the corresponding relationship in the map 107 in advance. For example, the corresponding relationship between the angle $\omega$ and the sight line error $\rho$ may be learned. In this case, a visual target capable of specifying the angle $\omega$ may be provided in advance, the corresponding relationship between the angle $\omega$ and the sight line error $\rho$ may be derived by viewing the visual target, and the derived corresponding relationship may be memorized in the map 107 in advance.

In addition, in each of the above embodiments, an example of the sight line direction estimation device including the distance sensor 18 that measures a distance to the head portion of an occupant has been described, but the sight line direction estimation device is not limited to including the distance sensor 18. For example, when the distance between the head portion of the occupant and the camera 16 is known and variation in the distance is within a predetermined distance range predicted to be less influenced by the estimation of the sight line direction, the predetermined distance between the head portion of the occupant and the camera 16 may be memorized in the sight line direction estimation device, and the memorized distance may be read out and used. In this case, it is preferable that a plurality of different distances are memorized stepwise and selectively, and a distance selected from the plurality of memorized distances is used.

A sight line direction estimation device according to an aspect of this disclosure includes: an imaging unit that captures an image of a head portion including an eyeball of a person; an eyeball center position calculation unit that calculates a center position of the eyeball using the image captured by the imaging unit; a pupil center position calculation unit that calculates an apparent pupil center position on an eyeball surface corresponding to a pupil center position of the eyeball using the image captured by the imaging unit; a sight line direction derivation unit that derives an apparent sight line direction in a direction connecting the eyeball center position and the apparent pupil center position; and a sight line direction estimation unit that estimates a sight line direction of the person based on the apparent sight line direction derived by the sight line direction derivation unit using a predetermined corresponding relationship between the sight line direction of the person connecting the eyeball center position and the pupil center position and the apparent sight line direction.

According to the sight line direction estimation device of the aspect of this disclosure, the eyeball center position calculation unit calculates the eyeball center position, and the pupil center position calculation unit calculates the apparent pupil center position on the eyeball surface corresponding to the pupil center position of the eyeball using the image captured by the imaging unit. The sight line direction derivation unit derives the apparent sight line direction in the direction connecting the eyeball center position and the apparent pupil center position. The sight line direction estimation unit estimates the sight line direction of the person corresponding to the apparent sight line direction using the predetermined corresponding relationship. The predetermined corresponding relationship indicates correspondence between the sight line direction of the person connecting the eyeball center position and the pupil center position and the apparent sight line direction. In this manner, since an actual sight line direction corresponding to the apparent sight line direction is estimated, the sight line direction can be estimated with a simple configuration by suppressing an influence caused by refraction caused by a cornea of the eyeball.

The eyeball center position calculation unit may calculate the eyeball center position based on a position of a characteristic point on a face around the eyeball on the captured image. In the captured image obtained by capturing the face including an eye, a characteristic region such as an outer canthus and an inner canthus, which characteristically represents the eye, is captured. It is assumed that a space between the outer canthus and the inner canthus corresponds to a size of the eyeball. Therefore, a center position of an eyeball model can be used as the eyeball center position by fitting the characteristic point on the face around the eyeball such as the outer canthus and the inner canthus to a predetermined eyeball model indicating a standard eyeball.

The eyeball center position calculation unit includes an irradiation unit that irradiates light and can calculate the eyeball center position based on a position of reflected light from the irradiation unit reflected by a surface of the eyeball. That is, the eyeball center position calculation unit can calculate the eyeball center position by a so-called cornea reflection method. In the cornea reflection method, the reflected light at the cornea is detected, and the eyeball center position is calculated from a positional relationship between a detected cornea position and the pupil center position included in the captured image.

The eyeball center position calculation unit can memorize the eyeball center position calculated based on the position of the characteristic point on the face and use the memorized eyeball center position. It may be difficult to always perform the calculation of the eyeball center position by the cornea reflection method. Therefore, the eyeball center position can be used without performing the calculation by the cornea reflection method usually by memorizing the calculated eyeball center position and using the memorized eyeball center position, and thus calculation load of the device can be suppressed.

The sight line direction estimation unit can estimate the sight line direction of the person using a map in which the sight line direction of the person connecting the eyeball center position and the pupil center position corresponds to the apparent sight line direction. In this manner, the sight line direction of the person can be estimated in a short time using the map in which the sight line of the person corresponds to the apparent sight line direction.

A sight line direction estimation method of this disclosure includes causing a computer to: calculate a center position of an eyeball using an captured image in which a head portion including the eyeball of a person is captured; calculate an apparent pupil center position on an eyeball surface corresponding to a pupil center position of the eyeball using the captured image; derive an apparent sight line direction in a direction connecting the eyeball center position and the apparent pupil center position; and estimate a sight line direction of the person based on the apparent sight line direction using a predetermined corresponding relationship between the sight line direction of the person connecting the eyeball center position and the pupil center position and the apparent sight line direction.

A sight line direction estimation program of this disclosure causes the computer to function as the sight line direction estimation device.

In this manner, the sight line direction can also be estimated by suppressing the influence caused by the refraction caused by the cornea of the eyeball according to the sight line direction estimation method and the sight line direction estimation program.

According to this disclosure as described above, it is possible to obtain an effect that the sight line direction can be estimated by considering the influence caused by the refraction caused by the cornea of the eyeball with a simple configuration.

Although this disclosure is described using the embodiments, a technical scope of this disclosure is not limited to a range described in the above embodiments. Various alterations or improvements can be applied to the above embodiments without departing from the spirit of this disclosure, and altered or improved embodiments are also included in the technical scope of this disclosure.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sight line direction estimation device comprising:
at least one processor configured to implement:
an imaging unit that captures an image of a head portion including an eyeball of a person;
a distance detecting unit that detects a distance between the imaging unit and the head portion;
an apparent sight line direction derivation unit that derives an apparent sight line direction connecting a center position of the eyeball and an apparent pupil center position on a surface of the eyeball corresponding to a pupil center position based on the image captured by the imaging unit and the distance between the imaging unit and the head portion;

a sight line direction estimation unit that estimates an actual sight line direction of the person based on a predetermined corresponding relationship between an actual sight line direction and the apparent sight line direction and the apparent sight line direction derived by the sight line direction derivation unit, the sight line direction estimate unit comprising:

a correction amount derivation unit configured to determine a correction amount from the apparent sight line direction to the actual sight line direction, the correction amount determined using corresponding relationship between the apparent sight line direction stored in a map and the correction amount to the actual sight line direction, wherein the actual sight line direction is estimated by correcting the apparent sight line, direction derived by the apparent sight line direction derivation unit with the correction amount derived by the correction amount derivation unit.

2. The sight line direction estimation device according to claim 1, wherein
the eyeball center position is derived based on a position of a characteristic point on a face around the eyeball on the captured image.

3. The sight line direction estimation device according to claim 1, wherein
the eyeball center position is derived based on a position of reflected light radiated from a light irradiation unit and reflected by the eyeball surface.

4. The sight line direction estimation device according to claim 3, wherein
the eyeball center position is derived using a center position of curvature of a cornea of the eyeball based on the position of the reflected light.

5. The sight line direction estimation device according to claim 1, wherein
the apparent sight line direction derivation unit derives the apparent sight line direction using an eyeball center position derived in advance and memorized in a memory unit as the eyeball center position.

6. The sight line direction estimation device according to claim 2, wherein
the apparent sight line direction derivation unit derives the apparent sight line direction using an eyeball center position derived in advance and memorized in a memory unit as the eyeball center position.

7. The sight line direction estimation device according to claim 3, wherein
the apparent sight line direction derivation unit derives the apparent sight line direction using an eyeball center position derived in advance and memorized in a memory unit as the eyeball center position.

8. The sight line direction estimation device according to claim 4, wherein
the apparent sight line direction derivation unit derives the apparent sight line direction using an eyeball center position derived in advance and memorized in a memory unit as the eyeball center position.

9. The sight line direction estimation device according to claim 1, wherein
the apparent sight line direction estimation unit includes:
an eyeball center position derivation unit that derives the eyeball center position based on the captured image; and
an apparent pupil center position derivation unit that derives the apparent pupil center position on an eyeball surface corresponding to the pupil center position of the eyeball based on the captured image.

10. The sight line direction estimation device according to claim 2, wherein
the apparent sight line direction estimation unit includes:
an eyeball center position derivation unit that derives the eyeball center position based on the captured image; and
an apparent pupil center position derivation unit that derives the apparent pupil center position on an eyeball surface corresponding to the pupil center position of the eyeball based on the captured image.

11. The sight line direction estimation device according to claim 3, wherein
the apparent sight line direction estimation unit includes:
an eyeball center position derivation unit that derives the eyeball center position based on the captured image; and
an apparent pupil center position derivation unit that derives the apparent pupil center position on an eyeball surface corresponding to the pupil center position of the eyeball based on the captured image.

12. The sight line direction estimation device according to claim 4, wherein
the apparent sight line direction estimation unit includes:
an eyeball center position derivation unit that derives the eyeball center position based on the captured image; and
an apparent pupil center position derivation unit that derives the apparent pupil center position on an eyeball surface corresponding to the pupil center position of the eyeball based on the captured image.

13. The sight line direction estimation device according to claim 5, wherein
the apparent sight line direction estimation unit includes:
an eyeball center position derivation unit that derives the eyeball center position based on the captured image; and
an apparent pupil center position derivation unit that derives the apparent pupil center position on an eyeball surface corresponding to the pupil center position of the eyeball based on the captured image.

14. A sight line direction estimation method comprising causing a computer to:
capture an image of a head portion including the eyeball of a person using an imaging unit:
determine a distance between the imaging unit and the head portion using distance detecting unit;
derive an apparent sight line direction connecting an eyeball center position and an apparent pupil center position on a surface of the eyeball corresponding to a pupil center position based on a captured image obtained by the capturing of the image of a head portion including the eyeball of a person and detecting of the distance between the imaging unit and the head portion; and
estimate an actual sight line direction of the person based on a predetermined corresponding relationship between the actual sight line direction of the person and the apparent sight line direction and the derived apparent sight line direction.

15. A sight line direction estimation device comprising:
at least one processor configured to implement:
the illumination unit that illuminations an eyeball;

an imaging unit that captures an image of a head portion including the eyeball of a person;

a distance detecting unit that detects a distance between the imaging unit and the head portion;

a first derivation unit that estimates an actual sight line direction of the person, including:

an apparent sight line direction derivation unit that derives an apparent sight line direction connecting a center position of the eyeball and an apparent pupil center position on a surface of the eyeball corresponding to a pupil center position based on the image captured by the imaging unit and the distance between the imaging unit and the head portion, and a sight line direction estimation unit that estimates an actual sight line direction of the person based on a predetermined corresponding relationship between an actual sight line direction and the apparent sight line direction and the apparent sight line direction derived by the apparent sight line direction derivation unit; and a second derivation unit that derives the sight line direction by a cornea reflection method, and derives the actual sight line direction of the person in consideration of refraction of light at the cornea surface using a captured image includes;

an eyeball center calculation unit that calculates an eyeball center position based on the captured image and includes a memory that memorizes information indicating the center position of the eyeball, a pupil center calculation unit that calculates a pupil center position of a pupil based on the captured image and performs a calculation of estimating a three-dimensional apparent pupil center position using the captured image from the imaging unit, and a sight line direction calculation unit that calculates the sight line direction using the eyeball center position and the three-dimensional apparent pupil center position, wherein the sight line direction estimation device is configured to switch from using the second derivation unit to the first derivation unit, when no corneal reflection is detected.

* * * * *